US00PP35099P2

(12) United States Plant Patent
Gitzels et al.

(10) Patent No.: US PP35,099 P2
(45) Date of Patent: Apr. 11, 2023

(54) ***DAHLIA* PLANT NAMED 'BALDADENAPR'**

(50) Latin Name: *Dahlia variabilis*
Varietal Denomination: Baldadenapr

(71) Applicant: Ball Horticultural Company, West Chicago, IL (US)

(72) Inventors: Jeroen Gitzels, Zwaag (NL); Jolanda Krassenburg, Wageningen (NL)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 17/989,214

(22) Filed: Nov. 17, 2022

(51) Int. Cl.
*A01H 5/02* (2018.01)
*A01H 6/14* (2018.01)

(52) U.S. Cl.
USPC ..... Plt./321

(58) Field of Classification Search
USPC ..... Plt./321
See application file for complete search history.

*Primary Examiner* — Susan McCormick Ewoldt
(74) *Attorney, Agent, or Firm* — Audrey Charles

(57) ABSTRACT

A new and distinct cultivar of *Dahlia* plant named 'Baldadenapr', characterized by its double-type, yellow-orange colored inflorescences, dark green-colored foliage, and moderately vigorous, upright growth habit, is disclosed.

1 Drawing Sheet

Latin name of genus and species of plant claimed: *Dahlia variabilis*.

Variety denomination: 'Baldadenapr'.

BACKGROUND OF THE INVENTION

The present invention relates to a new and distinct cultivar of *Dahlia* plant botanically known as *Dahlia variabilis* and hereinafter referred to by the cultivar name 'Baldadenapr'.

The new cultivar originated in a controlled breeding program in in Odense, Denmark during July 2016. The objective of the breeding program was the development of *Dahlia* cultivars that are freely flowering with large inflorescences, mid-season flower timing, and a moderately vigorous, upright growth habit.

The new *Dahlia* cultivar is the result of open pollination. The female (seed) parent of the new cultivar is the proprietary *Dahlia variabilis* breeding selection coded 17-497, not patented, characterized by its semi-double, medium bronze-colored inflorescences, medium green-colored foliage, and moderately vigorous, mounded growth habit. The male (pollen) parent of the new cultivar is unknown. The new cultivar was discovered as a single flowering plant within the progeny of the above stated open pollination during July 2017 in a controlled environment in in Odense, Denmark.

Asexual reproduction of the new cultivar by terminal stem cuttings since July 2017 in in Odense, Denmark, Hem, The Netherlands and Andijk, The Netherlands has demonstrated that the new cultivar reproduces true-to-type with all the characteristics, as herein described, firmly fixed and retained through successive generations of such asexual propagation.

SUMMARY OF THE INVENTION

The following characteristics of the new cultivar have been repeatedly observed and can be used to distinguish 'Baldadenapr' as a new and distinct cultivar of *Dahlia* plant:

1. Double-type, yellow-orange colored inflorescences;
2. Dark green-colored foliage; and
3. Moderately vigorous, upright growth habit.

Plants of the new cultivar differ from plants of the female parent primarily in having more ray florets per inflorescence and a yellow-orange colored inflorescence that is different from the bronze-colored inflorescence of the female parent.

Of the many commercially available *Dahlia* cultivars, the most similar in comparison to the new cultivar is DALAYA Yellow+Red Eye 'KLEDH13033', U.S. Plant Pat. No. 26,741. However, in side-by-side comparison, plants of the new cultivar differ from plants of 'KLEDH13033' in at least the following characteristics:

1. Plants of the new cultivar have larger diameter inflorescences than plants of 'KLEDH13033';
2. Plants of the new cultivar have more ray florets per inflorescence than plants of 'KLEDH13033'; and
3. Plants of the new cultivar have a ray floret color that is yellow-orange and different from the yellow and reddish-orange color of plants of 'KLEDH13033'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Baldadenapr'. The 4-month-old plants were grown in 6.5-inch pots for 10 weeks in a glass-covered greenhouse in Hem, The Netherlands. Plants were given one pinch before transplant.

DETAILED BOTANICAL DESCRIPTION

Figure 1:
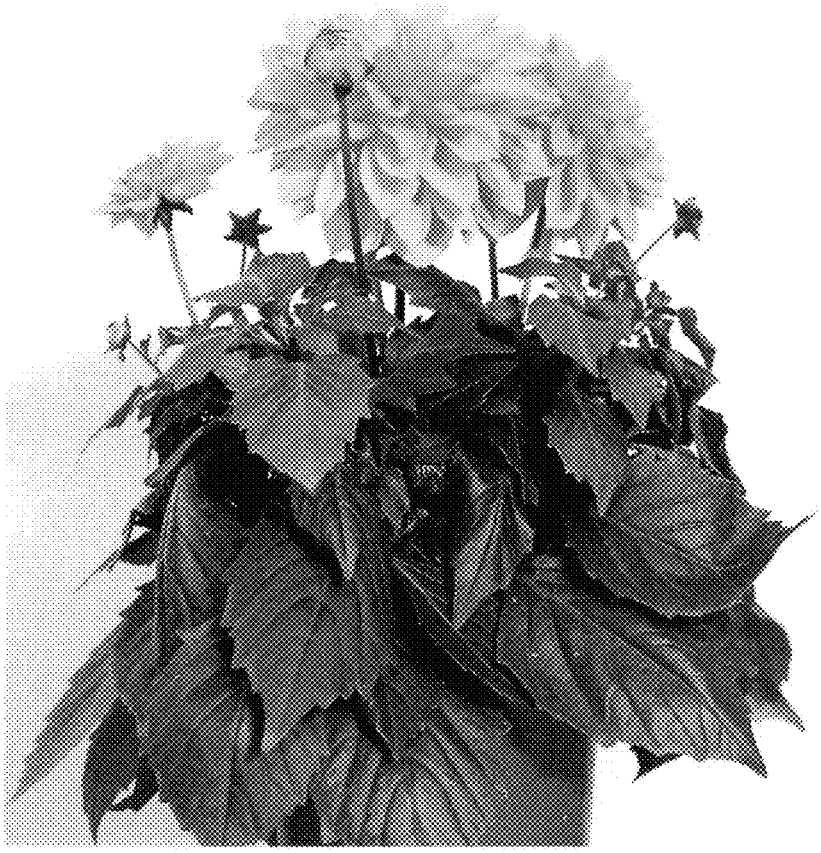
FIG. 1 illustrates a side view of the overall growth and flowering habit of 'Baldadenapr'.
Figure 2:
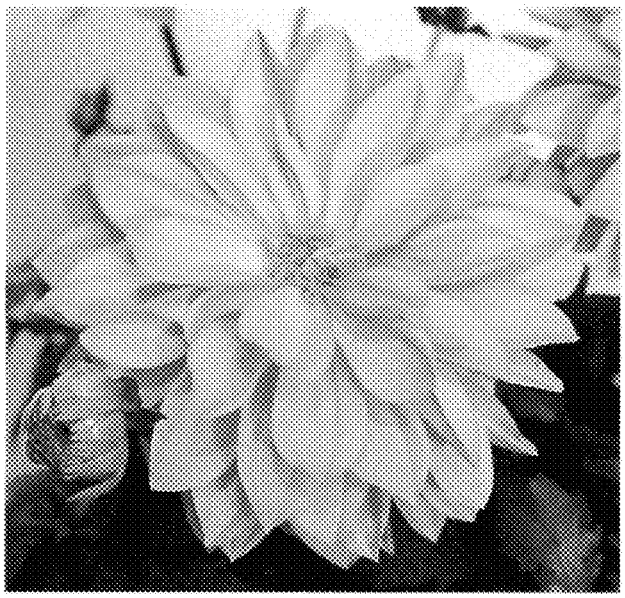
FIG. 2 illustrates a close-up view of an individual inflorescence of 'Baldadenapr'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in February 2022 under natural light conditions in Boskoop, The Netherlands.

The following descriptions and measurements describe 4-month-old plants produced from cuttings from stock plants and grown in a glass-covered greenhouse under conditions comparable to those used in commercial practice. The plants were grown in Hem, The Netherlands in 6.5-inch pots for 10 weeks utilizing a soilless growth medium. Plants were given one pinch before transplant. Greenhouse temperatures were maintained at approximately 61° F. to 72° F. (16° C. to 22° C.) during the day and approximately 57° F. to 61° F. (14° C. to 16° C.) during the night. Supplemental lighting was used. Measurements and numerical values represent averages of typical plants.

Botanical classification: *Dahlia variabilis* 'Baldadenapr'.

Parentage:

*Female parent.*—Proprietary *Dahlia variabilis* breeding selection coded 17-497, not patented.

*Male parent.*—Unknown.

Propagation:

*Type cutting.*—Terminal stem.

*Time to initiate roots.*—Approximately 9 to 12 days.

*Time to produce a rooted cutting.*—Approximately 25 to 32 days.

*Root description.*—Fine, fibrous.

*Rooting habit.*—Freely branching.

Plant description:

*Commercial crop time.*—Approximately 7 to 9 weeks from a rooted cutting to finish in a 15 cm pot.

*Growth habit and general appearance.*—Moderately vigorous, upright.

*Size.*—Height from soil level to top of plant plane: Approximately 28.2 cm. Height from soil level to top of foliage: Approximately 21.0 cm. Width: Approximately 35.5 cm.

*Branch.*—Quantity of lateral branches per plant: Approximately 11. Strength: Moderately strong. Length of lateral branch: Approximately 12.6 cm. Diameter of lateral branch at central internode: Approximately 6.0 mm. Length of central internode of lateral branch: Approximately 2.8 cm. Texture: Glabrous, young stems with a moderate very short pubescence. Color: 146B slightly to moderately tinted with 178A, particularly towards the nodes and base.

Foliage description:

*General description.*—Quantity of leaves per lateral branch: Approximately 10. Type: Simple and compound. Quantity of leaflets per compound leaf: Approximately 3, trifoliate. Fragrance: Slightly spicy. Arrangement: Opposite. Aspect: Petiole mostly perpendicular angle to stem with blade slightly extending downward. Shape of leaf and leaflet: Elliptic to broadly elliptic or broadly ovate. Margin of leaf and leaflet: Widely serrate. Apex of leaf and leaflet: Acute. Base of leaf and leaflet: Attenuate. Venation pattern: Pinnate.

*Simple leaf.*—Length: Approximately 14.7 cm. Width: Approximately 8.2 cm. Texture of upper and lower surfaces: Sparsely strigose pubescent. Color of upper surface: NN137A blended with 147A. Color of lower surface: 191A to 191B. Length of petiole: Approximately 3.7 cm. Diameter of petiole: Approximately 3.0 mm. Texture of upper and lower surfaces of petiole: Glabrous, ciliate. Color of upper surface of petiole: 146B with 152A and a heavy overlay of 178A. Color of lower surface of petiole: 146B.

*Mature trifoliate leaf.*—Shape: Broadly ovate to deltoid in outline. Length of mature trifoliate leaf: Approximately 15.8 cm. Width of mature trifoliate leaf: Approximately 16.6 cm. Length of terminal leaflet: Approximately 14.0 cm. Width of terminal leaflet: Approximately 6.9 cm. Length of lateral leaflets: Approximately 8.3 cm. Width of lateral leaflets: Approximately 4.5 cm. Texture of upper and lower surfaces: Sparsely strigose pubescent. Color of upper surface: NN137A blended with 147A. Color of lower surface: 191A to 191B. Length of petiole of mature trifoliate leaf: Approximately 4.2 cm. Diameter of petiole of mature trifoliate leaf: Approximately 3.5 mm. Texture of upper surface of petiole: Very sparsely strigose pubescent. Texture of lower surface of petiole: Glabrous. Color of upper surface of petiole: 146B with 152A, heavily tinted with 178A. Color of lower surface of petiole: 146B.

Flowering description:

*Flowering habit.*—'Baldadenapr' is freely flowering under outdoor growing conditions with substantially continuous blooming from spring through autumn.

*Lastingness of individual inflorescence on the plant.*—Approximately 2 weeks.

Inflorescence description:

*General description.*—Type: Double, composite, consisting of multiple rows or ray florets, and disc florets, persistent. Aspect: Facing upward and outward. Arrangement: Terminal, arising from leaf axils on strong peduncles positioned over the foliage. Disc and ray florets arranged acropetally on a capitulum. Quantity per plant: Approximately 4. Fragrance: None detected. Shape: Hemispherical to near spherical when ray florets are fully open. Inflorescence diameter: Approximately 13.0 cm. Inflorescence depth: Approximately 10.2 cm. Disc diameter: Approximately 2.1 cm. Receptacle diameter at base: Approximately 1.1 cm. Receptacle depth: Approximately 4.0 mm. Receptacle color: 146B.

*Peduncle.*—Strength: Strong. Aspect: Erect. Length: Approximately 12.7 cm. Diameter: Approximately 4.0 mm. Texture: Glabrous. Color: 200B slightly tinted with and striped with 146A.

*Bud.*—Rate of bud opening: Generally takes 2 weeks for bud to progress from first color to fully open flower. Quantity per plant: Approximately 8.

*Bud just before opening.*—Shape: Oblate. Depth at first color: Approximately 1.4 cm. Diameter at first color: Approximately 2.0 cm. Texture: Glabrous. Color: Outer surface of the phyllaries 151B with base of 143B to 143C and apex tinted with 167B to 167C.

*Ray florets.*—Quantity per inflorescence: Approximately 100. Arrangement: Imbricate, in multiple whorls. Aspect: Slightly to moderately convex. Shape: Obovate. Margin: Entire. Apex: Acute. Base: Attenuate. Appearance: Matte, moderately velvety. Length: Approximately 5.8 cm. Width: Approximately 2.9 cm. Texture of upper and lower surfaces: Glabrous. Color of upper surface when first and fully open: 17C with base of 2A. Color of lower surface when first and fully open: 15A and 17C with base of 1A. Color of upper surface before senescence: 21A to 21B with base of 2A. Color of lower surface before senescence: 26A with base of 3C.

*Disc florets.*—Quantity per inflorescence: Approximately 50. Arrangement: Massed in center of inflorescence. Aspect: Erect. Shape: Tubular. Margin: Entire. Apex: 5 acute tips. Base: Fused. Length: Approximately 1.5 cm. Diameter at apex: Approximately 4.0 mm. Diameter at base: Approximately 1.0 mm. Texture: Glabrous. Color when fully open: 13A with midsection of 151C and 154D at base, translucent.

*Outer phyllaries.*—Quantity: Approximately 5. Aspect: Slightly twisted, strongly reflexed. Shape: Ovate to elliptic. Margin: Entire. Apex: Acute. Base: Truncate. Length: Approximately 1.6 cm. Width: Approximately 9.0 mm. Texture of upper and lower surfaces: Glabrous. Color of upper surface: NN137A. Color of lower surface: 137B with venation of NN137A.

*Inner phyllaries.*—Quantity: Approximately 1 per floret. Shape: Linear, imbricate. Margin: Entire. Apex: Broadly acute to obtuse. Base: Truncate. Length of outermost: Approximately 2.1 cm. Width of outermost: Approximately 7.5 mm. Length of innermost: Approximately 1.3 cm. Width of innermost: Approximately 5.0 mm. Texture of upper and lower surfaces: Glabrous. Color of upper and lower surfaces: 150B, translucent with 143A at base of outermost.

*Reproductive organs.*—Androecium: On disc florets. Stamen quantity: 5 per floret. Stamen length: Approximately 6.0 mm. Anther shape: Linear. Anther length: Approximately 4.0 mm. Anther color: 13B. Pollen amount: Abundant. Pollen color: N25C. Gynoecium: On disc florets. Pistil length: Approximately 1.0 cm. Stigma shape: 2 branched. Stigma length: Approximately 2.0 mm. Stigma width: Approximately 8.0 mm. Stigma color: 17A. Style length: Approximately 8.0 mm. Style color: 150C. Ovary length: Approximately 1.0 mm. Ovary color: 154D.

Seed and fruit production: Neither seed nor fruit production has been observed.

Disease and pest resistance: Resistance to pathogens and pests common to *Dahlia* has not been observed.

What is claimed is:

1. A new and distinct cultivar of *Dahlia* plant named 'Baldadenapr', substantially as herein illustrated and described.

* * * * *